United States Patent [19]

Ibsen et al.

[11] 4,204,978
[45] May 27, 1980

[54] TOOTH CRACK DETECTOR

[75] Inventors: Robert L. Ibsen; William R. Glace; William R. Reed, Jr., all of Santa Maria, Calif.

[73] Assignee: Den-Mat, Inc., Santa Maria, Calif.

[21] Appl. No.: 7,401

[22] Filed: Jan. 29, 1979

Related U.S. Application Data

[63] Continuation-in-part of Ser. No. 954,841, Oct. 26, 1978, abandoned, which is a continuation-in-part of Ser. No. 830,461, Sep. 6, 1977, abandoned.

[51] Int. Cl.$^2$ .................... C09K 3/00; G01N 19/08; G01N 31/00; A61C 19/00
[52] U.S. Cl. .................... 252/408; 23/230 B; 106/35; 73/104; 422/61; 424/2; 424/7; 433/217
[58] Field of Search .................... 424/2, 7; 23/230 B; 422/61; 252/408, 301.19; 73/104; 106/19, 22, 35; 32/1

[56] References Cited

U.S. PATENT DOCUMENTS

| | | | |
|---|---|---|---|
| 2,151,495 | 3/1939 | Bender | 424/7 |
| 2,259,400 | 10/1941 | Switzer | 73/104 |
| 2,925,365 | 2/1960 | Nicholson et al. | 424/7 |
| 2,953,530 | 9/1960 | Switzer | 73/104 |
| 3,028,338 | 4/1962 | Parker, Jr. | 73/104 |
| 3,114,039 | 12/1963 | Switzer | 73/104 |
| 3,309,274 | 3/1967 | Brilliant | 424/7 |
| 3,436,453 | 4/1969 | Vincent, Jr. et al. | 424/7 |
| 3,553,311 | 1/1971 | Smith | 424/7 |
| 3,992,515 | 11/1976 | Johnson | 424/7 |

FOREIGN PATENT DOCUMENTS 1388531 3/1975 United Kingdom ............... 73/104

OTHER PUBLICATIONS

Magnaflux Corp. Advertisement, "Spotcheck-Hy-Rez," High Resolution Penetrant Kit, (1965).
Kasloff, et al., J. Pros. Dent., pp. 1166-1175, (Nov.–Dec. 1962).
Viener, Oral. Surc. Oral. Med. Oral. Path., pp. 594-595, (Nov. 1975).
Standlee et al., J. Pros. Dent., pp. 185-192, (Aug. 1970).
Dilts et al., J.A.D.A., vol. 81, pp. 387-391, (Aug. 1970).

*Primary Examiner*—Teddy S. Gron
*Attorney, Agent, or Firm*—Owen, Wickersham & Erickson

[57] ABSTRACT

A composition for detecting normally invisible cracks and splits in teeth, both in situ or in vitro. A detector solution contains a dye adapted to selectively stain such cracks and splits, advantageously methyl violet, a small amount of a surfactant, preferably dioctyl sodium sulfosuccinate, and a small amount of an acid, preferably glacial acetic acid, the remainder essentially water. A kit provides a holder or container and, at least one bottle containing such detector solution and one bottle containing a solvent for removing detector solution after the completion of the test. A preferred kit provides, in addition to the dye-removing solvent, two bottles, one containing solvent and dye, the other one containing solvent, surfactant, and acid, and equal amounts from each of these two bottles are mixed just before use on a patient. A method of selectively staining and detecting normally invisible cracks and splits is also provided.

24 Claims, 1 Drawing Figure

U.S. Patent May 27, 1980 4,204,978
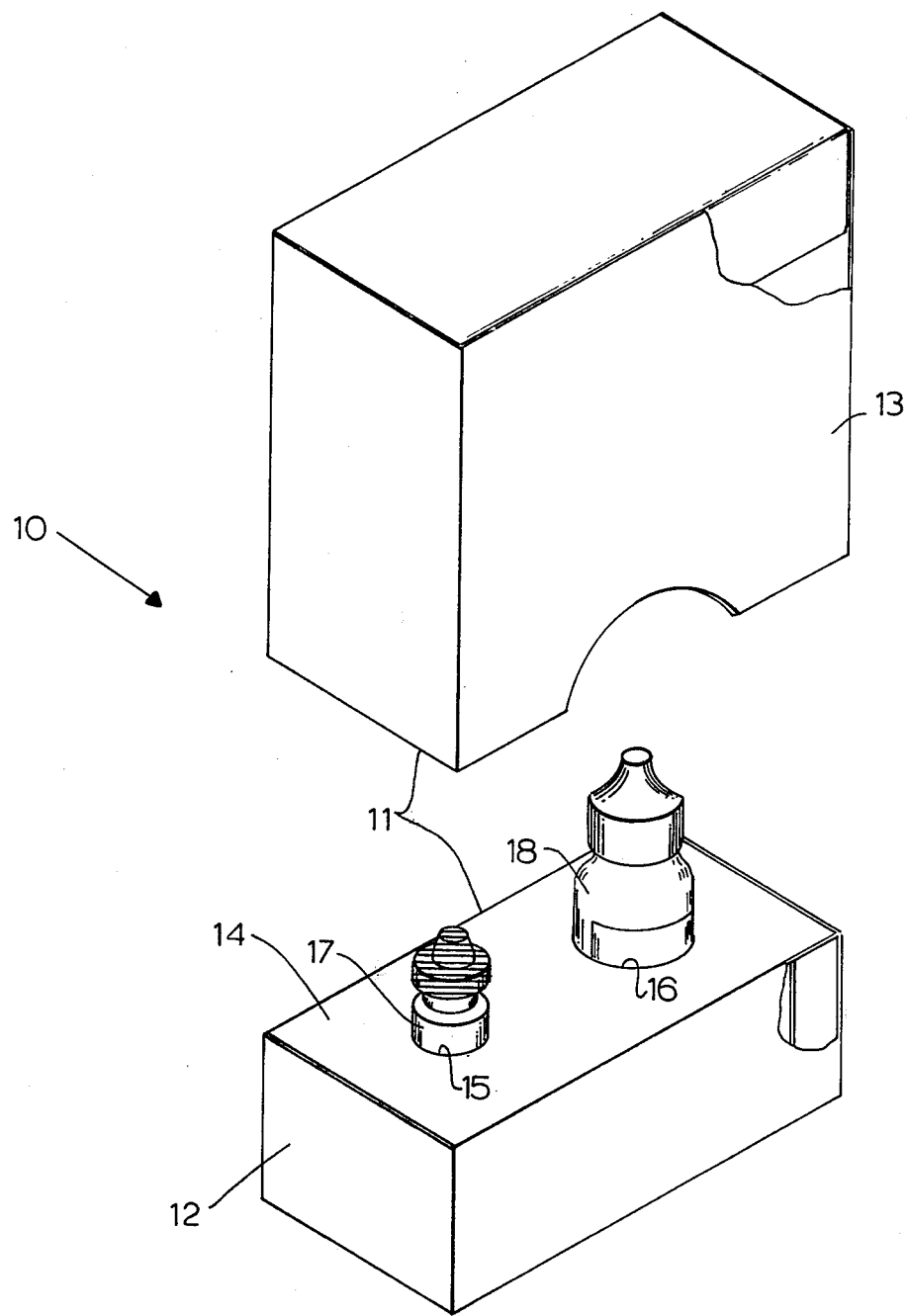

TOOTH CRACK DETECTOR

REFERENCE TO RELATED APPLICATION

This application is a continuation-in-part of application Ser. No. 954,841, filed Oct. 26, 1978, now abandoned, which was a continuation-in-part of application Ser. No. 830,461, filed Sept. 6, 1977, now abandoned.

BACKGROUND OF THE INVENTION

This invention concerns a composition for detecting cracks in teeth, being especially useful in diagnosing this problem in areas where such damage is difficult to observe directly and where hairline cracks exist. The invention also pertains to a method for carrying out such detection and to a kit which is portable and contains the components necessary for the dentist to carry out such detection.

Cracks can occur in teeth in various ways. They can be minute or obscure and thus seldom detected by previous known methods. Typically, they are not visible to the eye, either in ordinary light or ultraviolet light. They are usually invisible. Often, they do not show up at all in radiographs, because they are so oriented so as to be not detectable in view of the direction in which a radiograph is taken, or because the two segments are held closely together, whereas the radiograph can detect only differences in density. Crazing may occur in teeth but will not stain unless they become cracks.

However, such cracks can cause very great pain to the patient. For instance, upon chewing or even in merely closing the jaws, that is, under any pressure at all, a split tooth can cause extreme pain. At the same time, the crack, because of the close proximity of parts is puzzling to the dentist, who cannot see the crack. Not only chewing or pressure, but other conditions also, can cause pain or discomfort. For instance, the cracked tooth can be sensitive to sweet or sour tastes, or to heat or cold. Often, it is not possible for the patient to know exactly which tooth is affected, and the difficulty of diagnosis and treatment in such instances is obvious.

A split tooth can be caused by great depth of cavity preparation whereby later chewing on the filled tooth can create pressures resulting in a crack in the tooth. Another cause of such splitting or cracking can be the placement of a friction-lock pin which is intended to anchor a restoration and which can create under stresses in the tooth structure into which it is threaded. As patients age, the teeth become more brittle, and a tooth that has never been filled may crack. Cutting tools can also cause cracks. The patient may experience severe pain on chewing, but with or without an X-ray, no crack may be apparent, unless the crack goes completely through the tooth and a gross separation occurs. However, it is then too late to save the tooth, or that portion that has cracked away. On the other hand, cracks which have not completely fractured through a portion of the tooth are almost impossible to determine visually.

Once the existence and location of a split or crack is determined, it is relatively easy to give the patient relief. For example, by placing a cast crown or inlay restoration to protect the tooth from stress. The pain or discomfort is immediately relieved so long as the tooth is otherwise healthy, and the point of the fracture line is removed so as to stop the crack's progress.

The difficulty has heretofore lain in detecting the split or crack, and the present invention provides a composition, kit, and method which enables ready detection of such tooth failures. Thus, the diagnostic procedure is improved and accelerated. Also, this innovation provides the possibility of detection of splits or cracks with no discomfort to the patient.

SUMMARY OF THE INVENTION

The present invention provides a composition or solution for detecting, or revealing, the presence and location of normally invisible cracks or splits in a tooth, or even marginal leaks in a restoration, and a method for carrying out such detection, as well as a kit to enable the operator to carry out the detection.

The detector solution of the present invention is an acidic aqueous solution containing a dye or coloring agent which is adapted selectively to color cracks or splits in a tooth, and a surfactant compatible therewith and with the mouth environment and tissues. The surfactant enables the dye to flow and coat the surface of the suspected damaged area of such tooth. The remainder of the solution is substantially all water containing a small amount of a weak acid, such as acetic acid, citric acid, phosphoric acid, and the like, to provide a pH of the solution of from 1.0 to 6.5. For use on teeth in a patient's mouth, non-toxic components are employed.

The dye which is useful in the detector solution can be methyl violet, crystal violet, gentian violet, malachite green, erythrosin B, or acid fuchsin. Methyl violet and malachite green have been found most satisfactory of the dyes mentioned above, and methyl violet is especially advantageous, readily providing good color and good definition of the damaged area. The dye is present in the detector solution in an effective amount to selectively stain the cracks. There can be employed from about 0.01% by weight up to about 5% by weight of dye, these percentages being based on the total weight of the solution. More of the dye could be used, if desired, but would be wasteful and about 0.2 to about 1.25% of the dye by weight of the solution gives the best results.

The surfactant which is used is suitably dioctyl sodium sulfosuccinate or iso-octyl phenoxy polyethoxy ethanol, available in commerce under the trade name of Triton X-100. For treating teeth in situ, that is, in the patient's mouth, dioctyl sodium sulfosuccinate (DSS) is preferred because it has been approved by the U.S. Food and Drug Administration for use in the human body. However, iso-octyl phenoxy polyethoxy ethanol, containing 10 mols ethylene oxide, is also an effective surfactant and can be preferably used outside of the mouth, as in testing removable dentures. Other compatible surfactants, such as sodium lauryl sulfate, can alternatively be used. The surfactant is present in the solution in an amount of from about 0.05% to about 5%, preferably about 1.25%, by weight based on total weight of the solution. The surfactant should be compatible with the other components of the detector solution and also with the mouth environment in which it will be used. That is, in the mouth it should be non-toxic as used, and not harmful to the tissues, as well as not disagreeable in taste or odor.

The remainder of the solution is preferably water, slightly acidified to a solution pH of from 1.0 to 6.5, as defined above, or the remainder of the solution may be an organic liquid solvent, such as acetone, or a mixture of water and a water-miscible solvent. A fifty-fifty mixture of water and isopropyl alcohol aids getting the dye into solution. One very good embodiment of such remainder is water containing about 1% by weight, based on the total weight of the solution, of a weak acid, for instance, glacial acetic acid. Other acids can be used, such as citric acid, phosphoric acid, or any substantially non-toxic acid capable of adjusting the solution to the desired pH.

The solution so far described appears to have a useful shelf life of about one year; then there appears to be a degradation of the dye, possibly because of a reaction with the surfactant, since both the dyeing ability and the surfactant ability of the solution seem to disappear simultaneously. Where the solution is to be kept for more than a year, it is preferred to store it as two solutions, one containing the dye, the other the surfactant and acid. In this instance, the dye may be dissolved, for example, in water alone or it may, as a convenience in manufacture, be dissolved in a mixture of equal parts of water and isopropyl alcohol. The surfactant and acid may be dissolved in water alone.

When the solution is applied to the tooth and excess dye removed, the crack or split in the tooth becomes visible, because it is selectively stained in the sense that it takes on a deeper color than the intact surface of the tooth. The smooth, non-porous enamel tooth surface acquires some color, but the inner portion of the tooth, which is exposed by the crack or split, is more porous and therefore more absorptive, and the deeper penetration into the cracked surface may exhibit a deeper color. Whatever the reason or exact mode of operation, in the method of this invention the crack or split is clearly distinguished from the rest of the tooth. In addition, the stain or dye is more readily removed from the smooth enamel surface than from the crack or split margins.

It is an advantage of this invention that the composition which is provided enables rapid identification and location in teeth of cracks or splits which have been difficult or impossible to detect by earlier available methods. It is a further advantage that a kit is provided which facilitates the operator's identification of such cracks or splits in a rapid manner. The invention also teaches an advantageous method for the rapid and certain discovery of fractures in any part of a tooth to enable quick relief for a patient.

BRIEF DESCRIPTION OF THE DRAWINGS

In the drawings:

The FIGURE is an isometric view of a kit according to the present invention, including the detector or dye solution in its container and the cleaning solvent in its container.

DETAILED DESCRIPTION OF THE INVENTION

EXAMPLE 1

An excellent composition for detecting the aforementioned fractures in teeth, according to this invention, is an aqueous solution of methyl violet 2B (defined by "The Merck Index", Seventh Edition, as "A mixture of the more highly methylated fuchsins, principally pentamethyl-p rosaniline chloride."), and, as surfactant, dioctyl sodium sulfosuccinate, with a small amount such as about 1% by weight of the solution of a weak acid to provide an acid solution.

As an example of the methyl violet-containing solution, an acidified, low surface-tension solvent was made up as follows:

Distilled water: 200 grams
Glacial acetic acid: 2 grams
Dioctyl sodium sulfosuccinate: 2.5 grams Test solutions were made using the above solvent and the following dyes, each in an amount of 0.5% by weight, based on the weight of the solution:

| Test No. | Dye |
|---|---|
| 1 | Erythrosin B |
| 2 | Methyl green |
| 3 | Red food coloring (a composition approved by the F.D.A.) |
| 4 | Blue food coloring (a composition approved by the F.D.A.) |
| 5 | Cresol red |
| 6 | Methylene blue |
| 7 | Methyl violet |

The above test solutions were examined by dipping, for about 2 minutes in each, teeth cracked in the laboratory, then draining the teeth, sponging with water to remove excess dye and observing the disclosure of cracks. In this test, methyl violet was found to be most satisfactory, having provided sharp outlines of cracks which were theretofore invisible, and the teeth treated therewith were satisfactorily cleaned of the dye by sponging with a drying organic solvent, in this instance, a commercially available dental drying agent.

It should be remembered that in vitro testing is not directly comparable to in vivo use.

For in vivo use, the tooth is dried, and a cotton pellet containing the dye solution is applied to the tooth and allowed to remain against the tooth surface for from 20 to 60 seconds. Then a dry cotton pellet is used to remove the excess dye solution from the tooth surface. A crack shows by a line where the penetrated dye is not wiped off.

Later tests have shown that only marginal results are obtained in vivo from red food coloring, blue food coloring, methyl green, methylene blue, and cresol red in acid solution. We have also found that fluorescein green, methyl red, and quinidine red are also able to give only marginal results. By marginal results we mean that they produced some delineation of cracks but not enough that they could be completely relied on, as can methyl violet, erythrosin B, and methyl green.

EXAMPLE 2

Similar tests showed that gentian violet, crystal violet, and acid fuchsin gave satisfactory results when applied in the same manner.

EXAMPLE 3

Five test solutions of methyl violet 2B in the above surface tension solvent were made, adding, respectively, 0.2%, 0.3%, 0.4%, 0.6%, 0.8%, and 1.0% by weight (based on the total weight of the solution) methyl violet. These solutions were tested as in Example 1, and best results were obtained at 0.3% methyl violet.

EXAMPLE 4

A 0.3% solution of malachite green in the solvent of Example 1 was tested, as in Example 1, and good results were obtained.

EXAMPLE 5

A test solution was prepared using 1.0% by weight methylene blue in the above solvent. Portions of this solution were tested on teeth by several dentists and were found to disclose cracks, but it was not as satisfactory as the methyl violet solution because adherence of the dye to hard tooth surfaces prevented disclosure of the crack. There was insufficient contrast because the dye was not easily removed and did not come off the tooth surface when the dry cotton swab was used to wipe off that surface; hence cracks do not show up.

Similar tests using Triton X-100, i.e., iso-octyl phenoxy polyethoxy ethanol containing 10 mols of ethylene oxide, instead of DSS, gave like results in the assignee's laboratory.

EXAMPLE 6

Certain dyes were tested by preparing 1% by weight solutions thereof in (A) water and in (B) acetone. The solutions were tested by dipping laboratory-cracked teeth therein for about two minutes, then draining the teeth, sponging with water to remove excess dye, and observing disclosed cracks. The results were as follows:

| Dye | A<br>Water | B<br>Acetone |
| --- | --- | --- |
| Quinidine red | Faint | Fair |
| Fluorescein green | No action | Marginal |
| Crystal violet | Good | Fair |
| Methyl red | Faded quickly | No |

For oral use, water is a preferred solvent. The dyes tested, while operable, were in some instances more effective in acetone solution, a preferred organic solvent, as can be seen from the above listing. In general, those dyes which showed good results in water showed better results in acidified water with surfactant. Those showing relatively poor results in water were also relatively poor in acidified water with surfactant, although the performance of all dyes was improved in acidified water with surfactant. The importance of the surfactant and acid is greater when applied to a patient, where the teeth are treated directly in the mouth and where soaking in a dye solution is not practical.

EXAMPLE 7

Some advantageous results are obtained by incorporating a thickening or thixotropic agent in the dye solution, to limit flow during application. For example, methyl cellulose has been added at 6% of the total weight of the solution and at 10% thereof, both with good results. The solution was more viscous and so did not tend to run away rapidly, so that the solution remained in place longer, thereby increasing the probability of penetration.

Similar results were obtained with other thickening agents, including Aerosil (microcrystalline silica) at 10% by weight of the solution and other brands of microcrystalline silica.

EXAMPLE 8

When the stock dye-surfactant solution is only rarely used, it tends to deteriorate fairly rapidly when stored at room temperature for more than one year. Deterioration may be slowed down by keeping the dye and surfactant in different bottles, each at a concentration about double that eventually desired, with mixture of the two made just before use.

For example, one bottle may contain a 0.6% solution of methyl violet in water or in a mixture of equal parts of water and isopropyl alcohol. The isopropyl alcohol makes it easier to get the dye into solution.

Another bottle may contain an aqueous solution of acetic acid—about 2% by weight of glacial acetic acid—and surfactant, e.g., about 2½% by weight of dioctyl sodium sulfosuccinate.

Both bottles may be provided with drop-tops, and just before use, the detector solution may be prepared by placing one drop from each bottle in a Dappan dish and mixing. Use then proceeds as for the single solution.

Thickening agent may be added to either or both solutions.

EXAMPLE 9

In carrying out the methods of this invention on teeth in situ, the suspected area of the tooth, whether at the surface or within a prepared cavity, can be treated with the detector solution of the invention, for instance, such as that shown in Example 1 containing methyl violet, glacial acetic acid dioctyl sodium sulfosuccinate, remainder distilled water, as follows:

(1) The suspected area and the tooth are thoroughly dried.

(2) The suspected area is coated with the detector solution, suitably with a cotton pellet.

(3) The solution is allowed to remain on the tooth for up to about two minutes, preferably 20 to 60 seconds.

(4) The solution is wiped from the tooth with a dry cotton pellet.

(5) If a crack exists, it will show as a blue line.

(6) To remove almost all remaining detector solution from the cracks (and from plaque and debris, if any is present) the tooth is wiped with a cotton pellet soaked in solvent similar to or the same as that carrying the dye.

EXAMPLE 10

An excellent dye-removal solution is made as follows:

| Ingredient | Parts by Weight |
| --- | --- |
| Water | 100 |
| Citric acid | 4 |
| Surfactant (e.g., dioctyl sodium sulfosuccinate) | 6 |
| | 110 |

The crack detector may stain the soft tissue but will disappear in a short time. The detector solution is difficult to remove from composite restorations, however.

The drawing shows a kit 10 which provides the necessary materials for the dentist to carry out the method of this invention, the kit 10 comprising a container 11, which may be made up of a base member 12 and a closure means, in this instance a lid 13, which fits over the base member 12 and its contents. The base member 12 may be a box-like member having an upper surface 14 provided with two openings 15 and 16, to provide receptacles. Into one opening or receptacle 15 is inserted a bottle 17 containing detector solution; and into the other opening or receptacle 16 is fitted a larger bottle 18 containing solvent for removing color after treatment. This kit 10 is portable, is storable, and is convenient for dentists' use.

For the two-solution system, the bottle 17 contains the dye solution of Example 8, while the bottle 18 contains the solution of surfactant and acid, which is then used both in conjunction with the dye solution, as in Example 8, and also as solvent to remove the dye after the detection test has been performed. Both bottles preferably have caps provided with dropping members.

It will be understood that the above specific description and examples have been given for purposes of illustration only, and that variations can be made therein by one skilled in the art without departing from the spirit and scope of the appended claims. Parts or percentages given herein are by weight and are based, for instance, on the total weight of the solution or composition.

We claim:

1. A tooth crack detection composition for detecting ordinarily invisible cracks in a tooth in situ and in vitro, consisting essentially of:
   a dye chosen from the group consisting of methyl violet, crystal violet, gentian violet, malachite green, erythrosin B, and acid fuchsin, in a solvent consisting essentially of water or a non-toxic organic solvent for such dye,
   a small but effective amount of from about 0.05% to about 5% by weight of said solution of a non-toxic surfactant to cause the composition to coat the suspected area of a tooth, and
   a small amount of a non-toxic weak acid to provide a pH of the solution of about 1.0 to 6.5,
   said dye being present in said solution in an amount of from about 0.01% to about 5% by weight of said solution, sufficient to selectively color said cracks, and from zero to about 10% of a compatible non-toxic thickening agent.

2. A composition as in claim 1 wherein said dye is methyl violet.

3. A composition as in claim 2 containing about 0.3% of said dye.

4. A composition as in claim 1 wherein said surfactant is dioctyl sodium sulfosuccinate.

5. A composition as in claim 1 wherein said surfactant is present in an amount of about 1.25% by weight of said solution.

6. A composition as in claim 1 wherein said solution contains the compatible thickening agent in an amount of about 6% by weight.

7. The composition of claim 1 wherein said thickening agent is methyl cellulose.

8. A composition as in claim 1 wherein said acid is glacial acetic acid in an amount of about 1.25% by weight.

9. A kit for preparing the tooth crack detection composition of claim 1 comprising two separately stored solutions, one containing the dye, the other containing the acid and surfactants, for mixture just before the time of application to the tooth, thereby prolonging the shelf life of the ingredients.

10. The kit of claim 9 wherein the amounts of dye, acid, and surfactant in each solution are each double the amount used in the final solution, so that an equal mixture of the two solutions produces the amounts specified for the final solution.

11. A tooth crack detection composition for detecting ordinarily invisible hairline cracks in a tooth in situ and in vitro, consisting essentially of:
   a dye chosen from the group consisting of methyl violet, crystal violet, gentian violet, malachite green, erythrosin B, and acid fuchsin, in aqueous solution in an amount of from about 0.01% to about 5% by weight of said solution,
   a small but effective amount of from about 0.5% to about 5% of the weight of said solution of compatible non-toxic surfactant to cause the composition to coat the suspected area of a tooth, and
   a small amount of a non-toxic weak acid to provide a pH of the solution of 1.0 to 6.5,
   said dye present in said solution being sufficient to color said cracks selectively and render them visible.

12. The composition of claim 11 wherein said aqueous solution contains up to 10% by weight thereof of a non-toxic thickening agent.

13. A composition for detecting ordinarily invisible cracks in teeth in situ and in vitro consisting essentially of a solution of about 0.3% by weight methyl violet, about 1.0% by weight glacial acetic acid and about 1.25% by weight dioctyl sodium sulfosuccinate, the remainder water.

14. A kit for preparing a tooth crack detection composition for detecting ordinarily invisible hairline cracks in a tooth in situ and in vitro consisting essentially of:
   (1) a first solution in a solvent chosen from the groups consisting of water and a mixture of water and isopropyl alcohol in equal parts, of a dye chosen from the group consisting of methyl violet, crystal violet, gentian violet, malachite green, erythrosin B, and acid fuchsin, in an amount from about 0.02% to about 10% by weight of said solution, and
   (2) a second solution in water of
      (a) a small but effective amount of from about 1% to about 10% by weight of non-toxic surfactant compatible with the chosen dye, and
      (b) a small amount of a non-toxic weak acid to provide, when equal amounts of the first and second solution are mixed together, a pH of the mixture of 1.0 to 6.5,
   said first and second solutions normally being stored separately and mixtures made as occasion demands in the amount then needed.

15. The kit of claim 14 wherein at least one of said two solutions contains a compatible, non-toxic thickening agent, in an amount giving up to 10% thereof by weight in the equal mixture.

16. A kit for detection or ordinarily invisible cracks in teeth in situ and in vitro comprising:
   a closable container, provided with a plurality of receptacles,
   a first bottle disposed within a receptacle and filled with a predetermined amount of a tooth crack detector solution adapted to identify said cracks and to accentuate margins thereof, said solution consisting essentially of a dye taken from the group consisting of methyl violet, crystal violet, gentian violet, malachite green, erythrosin B, and acid fuchsin, and a non-toxic solvent for said dye, said dye being present in an amount of from about 0.01% to about 5% by weight of said solution to selectively stain said cracks, a small amount of from about 0.05% to about 5% by weight of said solution of a compatible, non-toxic surfactant effective to cause said solution to coat a suspected area of said teeth, and a small amount of a non-toxic weak acid to adjust the pH of said solution to between 1.0 and 6.5, and disposed in a second receptacle, a second bottle containing a non-toxic dye-removing solvent for the dye in said first bottle.

17. A kit as in claim 16 wherein said surfactant is dioctyl sodium sulfosuccinate.

18. A kit as in claim 16 wherein said acid is glacial acetic acid.

19. A kit as in claim 16 where said solution contains up to about 10% by weight of a non-toxic thickening agent.

20. A kit as in claim 16 wherein said dye-removing solvent comprises substantially the same solvent as that used for the dye.

21. A kit as in claim 20 where said dye-removing solvent includes water, acetic acid, and surfactant.

22. A kit for preparing a tooth crack detection composition for detection of ordinarily invisible cracks in teeth in situ and in vitro, comprising:

a closable container having two receptacles, a first bottle disposed in one said receptacle and having a drop top and filled with a first solution in a solvent chosen from the group consisting of water and a mixture of water and isopropyl alcohol in equal parts, of a dye chosen from the group consisting of methyl violet, crystal violet, gentian violet, malachite green, erythrosin B, and acid fuchsin, in an amount from about 0.02% to about 10% by weight of said solution, and a second larger bottle disposed in a second said receptacle having a drop top and filled with a second solution in water of a small but effective amount of from about 1% to 10% by weight of non-toxic surfactant compatible with the chosen dye, and a small amount of a non-toxic weak acid to provide, when equal amounts of said first and second solution are mixed together, a pH for the mixture of 1.0 to 6.5.

23. The kit of claim 22 in which said surfactant is dioctyl sodium sulfosuccinate.

24. The kit of claim 22 in which said acid is acetic acid.

* * * * *